United States Patent
Rajashekara et al.

(10) Patent No.: US 6,495,334 B1
(45) Date of Patent: Dec. 17, 2002

(54) RECOMBINANT SEF14 FIMBRIAL PROTEIN FROM SALMONELLA

(75) Inventors: Gireesh Rajashekara, St. Paul, MN (US); Kakambi V. Nagaraja, Roseville, MN (US); Vivek Kapur, St. Anthony, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 09/230,078

(22) PCT Filed: Jul. 18, 1997

(86) PCT No.: PCT/US97/12639
§ 371 (c)(1),
(2), (4) Date: May 20, 1999

(87) PCT Pub. No.: WO98/03656
PCT Pub. Date: Jan. 29, 1998

Related U.S. Application Data (60) Provisional application No. 60/022,191, filed on Jul. 19, 1996.

(51) Int. Cl.[7] ............................................. G01N 33/554
(52) U.S. Cl. ................ 435/7.32; 424/139.1; 424/163.1; 424/164.1; 424/184.1; 424/185.1; 424/190.1; 424/234.1; 424/258.1; 435/4; 435/7.1; 435/7.2; 435/7.35; 435/252.8; 530/300; 530/350
(58) Field of Search ........................... 424/139.1, 163.1, 424/164.1, 184.1, 185.1, 190.1, 234.1, 258.1; 435/4, 7.1, 7.2, 7.32, 7.35, 252.8; 436/501; 530/300, 350

(56) References Cited

U.S. PATENT DOCUMENTS 5,510,241 A    4/1996   Thorns

FOREIGN PATENT DOCUMENTS

| WO | WO 92/06197 | 4/1992 |
| WO | WO 92/06198 | 4/1992 |
| WO | WO 93/20231 | 10/1993 |

OTHER PUBLICATIONS

Feutrier, J. et al., "Purification and Characterization of Fimbriae from *Salmonella enteritidis*", *J. Bacteriol.*, vol. 168, No. 1, pp. 221–227 (Oct. 1986).

Clouthier, S. et al., "Characterization of Three Fimbrial Genes,, sefABC, of *Salmonella enteritidis*", *Journal of Bacteriology*, vol. 175, No. 9, pp. 2523–2533 (May 1993).

Ogunniyi, A. et al., "A *Salmonella enteritidis* 11RX Pilin Induces Strong T–Lymphocyte Responses", *Infection and Immunity*, vol. 62, No. 12, pp. 5376–5383 (Dec. 1994).

Peralta, R. C. et al., "Passive immunisation against experimental salmonellosis in mice by orally administered hen egg–yolk antibodies specific for 14–kDa fimbriae of *Salmonella enteritidis*", *The Pathological Society of Great Britain and Ireland*, pp. 29–35 (1994).

Rajashekara, G. et al., "Application of Recombinant Fimbrial Protein for the Specific Detection of *Salmonella enteritidis* Infection in Poultry", *Diagn Microbiol Infect Dis*, vol. 32, pp. 147–157 (1998).

Rajashecara, G. et al., "A rapid strip immunoblot assay for the specific detection of *Salmonella enteritidis* infection in chickens", International Journal of Food Microbiology, 8 pages (1999).

Thorns, C. et al., "Characterisation of monoclonal antibodies against a fimbrial structure of *Salmonella enteritidis* and certain other serogroup D salmonellae and their application as serotyping reagents", *Research in Veterinary Science*, vol. 53, pp. 300–308 (1992).

Thorns, C. et al., "The use of latex particle agglutination to specifically detect *Salmonella enteritidis*", *International Journal of Food Microbiology*, vol. 21, pp. 47–53 (1994).

Thorns, C. et al., "Development and Application of Enzyme–Linked Immunosorbent Assay for Specific Detection of *Salmonella entertidis* Infections in Chickens Based on Antibodies to SEF14 Fimbrial Antigen", *Journal of Clinical Microbiology*, vol. 34, No. 4, pp. 792–797 (Apr. 1996).

Turcotte, C. et al., "Cloning, DNA nucleotide sequence and distribution of the gene encoding the SEF14 fimbrial antigen of *Salmonella enteritidis*", *Journal of General Microbiology*, vol. 139, pp. 1477–1485 (1993).

*Primary Examiner*—Rodney P Swartz
(74) *Attorney, Agent, or Firm*—Merchant & Gould P.C.

(57) ABSTRACT

A truncated SE fimbria antigen useful as an antigen for immunoassay diagnosis of *Salmonella enteritidis* (SE) infection or evidence of infection.

13 Claims, 7 Drawing Sheets

RECOMBINANT SEF14 FIMBRIAL PROTEIN FROM SALMONELLA

This application is a 371 of PCT US97/12639, filed Jul. 18, 1997, which claims priority to U.S. Provisional Application No. 60/022,191, filed Jul. 19, 1996.

FIELD OF THE INVENTION

The present invention relates to a method of cloning and expressing a truncated form of a fimbrial gene and the use of the truncated fimbrial gene product in an immunodiagnostic assay and for immunoprophylaxis.

BACKGROUND OF THE INVENTION

Foodborne infections cause an estimated 6.5 million cases of human illness and 9000 deaths annually in the United States alone. Bacterial infections by Salmonella are the most commonly reported cause of foodborne outbreaks. *Salmonella enteritidis* (SE) is the dominant Salmonella serotype isolated from cases of food poisoning. Many of these outbreaks are thought to be due to infected poultry products, particularly eggs and egg products.

The best way to prevent infection in human populations is to diagnose and treat the infected animal prior to human consumption. Because the greatest threat of food poisoning from Salmonella is from poultry products, there is a need for a method to detect birds that are infected with SE.

Some current diagnostic methods rely on conventional bacteriologic cultures. However, these procedures are relatively slow, often taking up to 3 to 4 days to provide even a presumptive diagnosis. Additionally, the great susceptibility of SE to physical and chemical factors such as desiccation, radiation, low temperature, heating, or chemical preservatives, causes traditional bacteriologic culture methods to generally have a low sensitivity. Consequently, many birds or animals that are infected with SE are often not detected when conventional bacterial cultures are used.

Other diagnostic methods rely on the detection of serum antibodies specific to SE. Although several serological methods such as micro-agglutination, serum plate agglutination, latex particle agglutination microantiglobulin, ELISA have previously been employed, these assays lack either the sensitivity or specificity necessary to detect SE infected birds, or the tests are too difficult to perform in a routine laboratory or field setting. Consequently, widespread application of these tests for the detection of SE infections has been impractical.

A useful antigenic determinant that is found on many species of Enterobacteriaceae are fimbriae, proteinaceous filamentous surface structures composed of protein subunits called fimbrin. Upon infection, birds make antibodies to this SE fimbrial antigen. Therefore, the SE fimbrial antigen is useful in a diagnostic assay for the presence of SE in poultry.

SE is known to have at least four distinct fimbria, designated Sef14, Sef17, Sef18 and Sef21. These proteins are encoded by SefA, AgfA, SefD and FinA genes, respectively.

Although the gene encoding Sef14 has been identified and its DNA nucleotide sequence determined (Trucotte and Woodward, *Journal of General Microbiology*, 139:1477–1485 (1993)), an effective diagnostic method using this surface antigen has not been developed, partially due to the difficulty of efficiently producing the fimbriae proteins in purified form and in large quantities. Additionally, expression of Sef14 fimbriae by cultured *Salmonella enteritidis* is highly dependent on the growth medium composition. In a study by Thorns et al., *International Journal of Food Microbiology*, 21:47–53 (1994), only peptone water pH 7.2 supported the expression of Sef14 by all *Salmonella enteritidis* strains examined. [Consequently, previous diagnostic assays using Sef14 have used antibodies against Sef14 and not the antigen itself.]

Thorns et al., *Journal of Clinical Microbiology*, 34(4):792–797 (1996),have disclosed an ELISA for the detection of *Salmonella enteritidis* based on antibodies to an uncharacterized fraction of cell lysates having SEF14 activity. This assay suffers from the problems previously mentioned. Thorns isolates SEF14 from harvested *Salmonella enteritidis* 486/86 (phage type 4) rendering the process highly dependent on the growth medium and susceptible to the difficulties in efficiently producing the fimbriae proteins in purified form and in large quantities.

Hence, there is a need for a sensitive, specific and routine antigen and method to reliably detect SE infection in birds, preferably a method that is easily adaptable to large-scale screening of poultry flocks.

The use of recombinant techniques as presented herein afford a process for efficiently producing a truncated or modified form of SEF14. The truncated or modified form of SEF14 is easily isolated to a high degree of purity in large quantities suitable for use in diagnostic assays for large-scale screening.

SUMMARY OF THE INVENTION

The present invention provides a sensitive, specific, routine antigen and assay to reliably detect SE-infected animals. Specifically, the present invention provides a truncated form of the Sef14 antigen that can be easily produced in purified form and in large quantities and used in the method of the invention. The novel Sef14 antigen, when coupled to a substrate such as latex beads, provides a diagnostic assay for SE, particularly useful in large-scale screening of poultry flocks.

DETAILED DESCRIPTION OF THE INVENTION

The present invention is directed to a method for diagnosing *Salmonella enteritidis* infection or evidence of infection in an animal, particularly poultry, using a recombinant truncated fimbrial antigen.

"Infection" means active colonization of the animal by SE organisms. "Evidence of infection" means a prior history of colonization by SE in the animal, although active colonization is not present. Diagnosis of active infection is needed to protect against contamination of food supplies, whereas diagnosis of prior infection is needed to alert against new infection or to trace the source of infection in a flock.

Fimbrial Proteins

Fimbriae are proteinaceous filamentous surface structures composed of protein subunits called fimbrin. These proteinaceous structures are thought to be virulence factors which mediate specific attachment to host cell mucosal surfaces. They are present in most enteric bacteria capable of invading host cells.

*Salmonella enteritidis* has four distinct fimbriae: Sef14, Sef17, Sef18 and Sef21 which are encoded by sefA, agfA, sefD and fimA genes, respectively. Sef14, is unique with only limited distribution in the genus. In contrast, all other fimbrial proteins are widely distributed in the genus. Thus, they have limited use as diagnostic reagents for SE detection.

Cloning and Expression of Sef14,

In the present invention, a truncated form of the Sef14 antigen retaining the antigenic character of the entire protein has been produced. Unlike the complete protein, however, the truncated form can be easily produced in purified form and in large quantities, without special growth medium requirements.

PCR technology is used to produce the truncated Sef14 protein by amplification with suitable primers.

Figure 1:
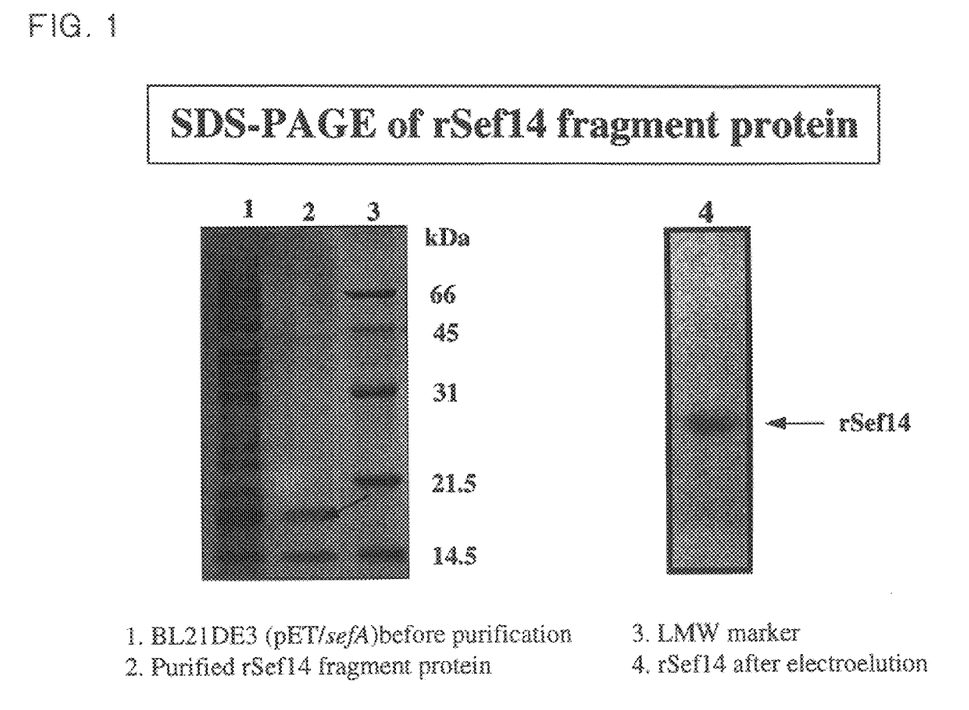
FIG. 1 is a photograph showing a SDS-PAGE of the recombinant Sef14 (rSef14) fragment (arrow).

Primers are selected to amplify the gene encoding Sef14 in a region downstream of the encoded signal peptide, e.g., downstream of about nucleotide 145 of the DraI genomic fragment shown in FIG. 1 of Turcotte and Woodward, Supra. Preferably, the PCR primers include, additional nucleotides at the 5' ends, specific restriction enzyme recognition sequences, for ease of purification. For example, useful primers for amplifying that portion of the sefA gene encoding an immunogenic Sef14 fragment downstream of the signal peptide are shown below:

```
GGGAATTCGCTGGCTTTGTTGGTAACA      SEQ ID NO:1

GGGCTCGAGTTAGTTTTGATACTGAACGTA   SEQ ID NO:2
```

After a truncated gene sequence encoding Sef14 is produced, it can be cloned into a host using a plasmid or phage as a vector. Typically, the expression of Sef14 fimbriae by cultured *Salmonella enteritidis* is highly dependent on the growth medium composition (Thorns et al, *International Journal of Food Microbiology,* 21:47–53 (1994)), and it is typically difficult to produce large quantities. However, a truncated form of Sef14 having at least the signal peptide removed is expressed in host systems such as *E. coli* without these difficulties.

Truncated Sef14 Antigen

Because the truncated Sef14 protein retains the antigenic characteristics of the complete protein, it is useful in various immunological methods. For example, the inventive antigen is useful in antibody binding immunoassays such as assays to detect the presence of antibodies against SE in a sample. Suitable binding assays include ELISA, wherein the recombinant Sef14 antigen is bound to a surface and exposed to antibodies against SE. To detect the presence of bound anti-SE antibodies, a marker such as an enzyme-linked secondary antibody is then added.

An agglutination assay using truncated Sef14 antigen-coated latex beads is preferred. In the agglutination reaction, antigen-coated latex beads form detectable clusters when exposed to antibodies against SE. This preferred assay is described more fully in Example 4, below.

Diagnostic Assays

The assays described above can be used to detect the presence of antibodies to *Salmonella enteritidis*. Preferably, the assays are used to determine whether or not an animal, e.g. a poultry animal such as a chicken or turkey, is infected with SE. Animal fluid such as blood or serum can be used in a diagnostic assay. If an animal is infected with SE, the animal will typically produce anti-SE antibodies. The recombinant Sef14 antigen is used to detect the presence of anti-SE antibodies, SE infection or the SE organism itself. Diagnostic assays such as these are particularly useful in birds. More particularly, diagnostic assays are useful in detecting SE infections in chicken or turkey to prevent foodborne illness by poultry consumption.

Vaccine

Passive immunization with anti-Sef14 antibodies has been shown to reduce *Salmonella enteritidis* colonization (Peralta et al. 1994). Additionally, Sef14 can induce a T-cell immune response (Ogunniyi et al 1994). Because the truncated Sef14 antigen exhibits these immunological activities, can be produced in large quantities, and does not have the cumbersome growth requirements of the complete protein, the truncated Sef14 antigen is also useful as a vaccine to confer immunity against SE. Preferably, the truncated Sef14 antigen is used as a vaccine in poultry to prevent foodborne illnesses.

EXAMPLES

The invention may be better understood with reference to the following examples which are not intended to limit the invention.

Example 1

Isolation of *S. enteritidis* Genomic DNA

*S. enteritidis* was grown overnight at 37° C. in Luria-Bertani (LB) broth. Genomic DNA was extracted as described (Sambrook, et al., 1989) using standard methods with minor modifications. In brief, bacterial cells were pelleted by centrifugation at 13,000×g for 3 minutes, washed/suspended in 1 ml of 1 M NaCl, centrifuged for 5 minutes at 13,000×g, and the pellet resuspended in 1 ml TE buffer (50 mM Tris-HCl, 50 mM EDTA, pH 7.8). The sample was next incubated with 5 μl of lysozyme (50 mg/ml) (Sigma Chemical Co., St. Louis, Mo.) and 0.3 mg/ml RNase A (Sigma) at 37° C. for 30 minutes. To this suspension, 1% sarkosyl and 0.6 mg/ml of proteinase K (Sigma) were added, and the mixture incubated at 37° for 1 hour. Following incubation, chromosomal DNA was extracted twice with an equal volume of phenol-chloroform-isoamyl alcohol (25:24:1) and once with chloroform:isoamyl alcohol (24:1). Genomic DNA in the aqueous phase was precipitated at −20° C. with two volumes of absolute ethanol and 0.1 volume of 3 M sodium acetate, and pelleted by centrifugation at 13,000×g for 5 minutes. The pellet was then washed twice with 70% ethanol, air dried, and suspended in TE Buffer (10 mM Tris-HCl and 1 mM EDTA pH 8.0). Total DNA was quantitated spectrophotometrically at $A_{260}$ nm.

Example 2

Cloning of sefA Gene Fragment
Oligonucleotide Primer Selection and Synthesis

Oligonucleotide primers corresponding to an internal fragment (64–498 bp) of the open-reading frame of the sefA gene were used for PCR amplification. Additional bases were added to the 5' end of each primer in order to confer a recognition sequence for either EcoRI (forward primer) or XhoI (reverse primer). The oligonucleotide primers were obtained from Integrated DNA technologies Inc., Ames, Iowa. The DNA sequences for the forward and reverse primers are shown below:

<u>GGGAATTC</u>GCTGGCTTTGTTGGTAACA          SEQ ID NO:1

<u>GGGCTCGAG</u>TTAGTTTTGATACTGAACGTA          SEQ ID NO:2

Additional nucleotides added to the 5' end of the primers are underlined.

PCR Amplification of sefA Gene Fragment

Amplification reactions were performed in 30 μl volumes with 30 pmol of each primer and 5 mM MgCl₂. The reagents and enzymes used for PCR were obtained either from Boehringer Mannheim (Indianapolis, Ind.) or Perkin Elmer (Foster City, Calif.). One hundred ng of genomic DNA was used as a template for PCR amplification with the following parameters: an initial denaturation at 94° C. for 5 minutes, followed by 35 cycles of denaturation (94° C. for 1.5 minutes), annealing 52° C. for 1 minute) and extension (72° C. for 2 minutes), and a final extension of 15 minutes at 72° C. All amplification reactions were performed in a Perkin-Elmer Cetus DNA thermal cycler (Model 480). The PCR products were analyzed on a 1% agarose gel, stained with ethidium bromide (0.5 μg/ml), and photographed under UV light.

PCR products were gel extracted (Qiagen Inc., Chatsworth, Calif.), quantitated spectophometrically, at 260 nm, and cloned directly into pGEM-T vector (Promega, Madison, Wis.). Following ligation, 2 μl of the reaction products were transformed into *E. coli* DH5α cells (Gibco BRL, Gaithersburg, Md.) by the heat shock method. Recombinant colonies were selected on ampicillin/IPTG-Xgal containing plates and screened for the presence of the appropriate insert by restriction analysis.

Nucleotide Sequence Analysis

A bacterial colony containing the recombinant plasmid with the rSefA fragment was grown in LB-ampicillin media, and the plasmid extracted using Qiagen plasmid extraction kit (Qiagen). The nucleotide sequence of the insert was determined using oligonucleotide primers specific to the vector sequence by automated DNA sequencing at the University of Minnesota Advanced Genetic Analysis Center. The insert was sequenced in its entirety in both orientations, and the amino acid sequence deduced using the standard genetic code (DNA*, Madison, Wis.). Sequencing results are shown below for nucleotide and deduced amino acid sequences of the insert (Seq.ID.NO:5), together with a tag sequence added during the subcloning of the fragment into the pET/abc expression vector (Seq.ID.NO:3). The added tag sequence at the 5' end, provides a Histidine-rich portion to facilitate purification of the sequence on nickel columns, as well as an antigenic region that specifically binds the T7 anti-tag antibody provided with the pET/abc vector kit.

Nucleic Acid Sequence Encoding rSefA Fragment
SEQ ID NO:3

<u>ATG GGC AGC AGC CAT CAT CAT CAT CAT CAC AGC AGC GGC CTG GTG</u> 45

<u>CCG CGC GGC AGC CAT ATG GCT AGC ATG ACT GGT GGA CAG CAA ATG</u> 90

<u>GGT CGC GGA TGG GAA TTC</u> GCT GGC TTT GTT GGT AAC AAA GCA GTG 135

GTT CAG GCA GCG GTT ACT ATT GCA GCT CAG AAT.ACA ACA TCA GCC 180

AAC TGG AGT CAG GAT CCT GGC TTT ACA GGG CCT GCT GTT GCT GCT 225

GGT CAG AAA GTT GGT ACT CTC AGC ATT ACT GCT ACT GGT CCA CAT 270

AAC TCA GTA TCT ATT GCA GGT AAA GGG GCT TCG GTA TCT GGT GGT 315

GTA GCC ACT GTC CCG TTC GTT GAT GGA CAA GGA CAG CCT GTT TTC 360

CGT GGG CGT ATT CAG GGA GCC AAT ATT AAT GAC CAA GCA AAT ACT 405

GGA ATT GAC GGG CTT GCA GGT TGG CGA GTT GCC AGC TCT CAA GAA 450

ACG CTA AAT GTC CCT GTC ACA ACC TTT GGT AAA TCG ACC CTG CCA 495

```
                                    -continued
GCA GGT ACT TTC ACT GCG ACC TTC TAC GTT CAG CAG TAT CAA AAC 540

TAA CTC GAG CCC 552
```
*Additional amino acid residues added to the amino terminus to
facilitate protein purification and cloning are underlined.

Deduced Amino Acid Sequence of rSefA Protein
Fragment* Seq. ID NO:4

MGSSHHHHHHSSGLVPRGSHMASMTGGOOMGRGSEFAGFVGNKAVVQAAVT

IAAQNTTSANWSQDPGFTGPAVAAGQKVGTLSITATGPHNSVSIAGKGASVSGG

VATVPFVDGQGQPVFRGRIQGANINDQANTGIDGLAGWRVASSQETLNVPVTT

FGKSTLPAGTFTATFYVQQYQN
*Additional amino acid residues added to the amino
terminus to facilitate protein purification and cloning
are underlined.

It is understood that the amino acids added to the N-terminus of the Spf14 antigen are optional, and used for ease of cloning and purification. The amino acid sequence in the absence of these added residues (Sequence ID No:6) with or without other added residues for cloning or purification procedures, for example, are similarly useful as antigens in the diagnostic assays of the invention.

Subcloning sefA Gene Fragment into an Expression Vector

The pGEM-T plasmid carrying sefA fragment was double digested with EcoRI and XhoI, and the digested products gel purified (Qiagen) and cloned into EcoRI and XhoI digested pET/abc expression vectors (Novagen Inc., Madison, Wis.). Ligation products (2 μl) from each of the reactions were transformed into *E. coli* BL21(DE3)pLyS cells by heat shock method. Recombinant clones were cultured on kanamycin and chloramphenicol containing plates, and analyzed by restriction enzyme analysis.

rSefA Fragment Expression

The recombinant clones were selected based on restriction enzyme analysis with EcoRI and XhoI digestion, selecting those clones yielding appropriately sized fragments as compared with a vector control. Selected clones were analyzed for rSefA fragment expression. Briefly, a single colony from each (pETabc/SefA fragment) freshly streaked plate was picked and inoculated to 50 ml LB broth containing appropriate antibiotics and incubated with shaking at 200 rpm at 37° C. until the $OD_{600}$ reached 0.6. Cultures were induced with IPTG (0.4 mM) and incubated for an additional 3 hours. Following incubation, the cells were pelleted and resuspended in 5 ml of TE buffer (50 mM Tris-HCl pH 8.0, 2 mM EDTA) and incubated with 25 μl of lysozyme (50 mg/ml) and 100 μl of 1% Triton X-100 for 20 minutes at 30° C. The samples were sonicated until they were no longer viscous, and centrifuged at 39,000×g for 20 minutes. The supernatant was passed through a 0.45 μm membrane filter, and stored at -20° C. until further use.

SDS-PAGE Analysis

The cell lysates were next analyzed by SDS-PAGE for the presence of the rSefA fragment by mixing with an equal volume of 2×SDS solubilization buffer separating on 2% polyacrylamide gels, and staining with Coomassie blue. The results are shown in lane 1 of FIG. 1 which contains the total protein produced by the vector and contained in the cell lysates.

Western Blot Analysis

Figure 2:
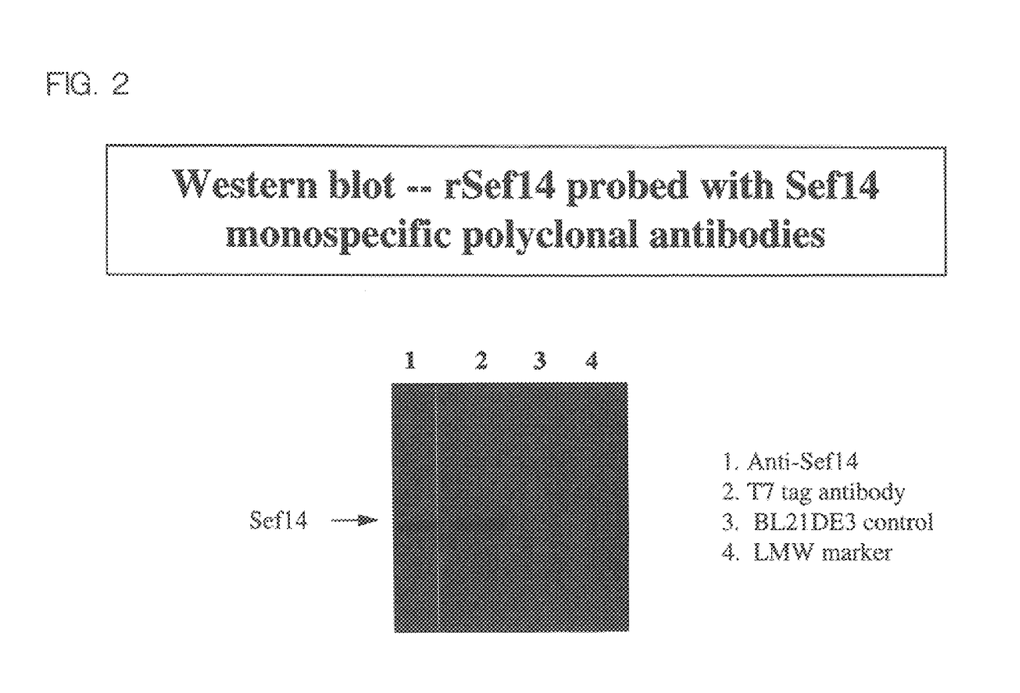
FIG. 2 is a photograph showing a Western blot of the rSef14 fragment probed with anti-Sef14 antibody (lane 1) and anti-tag (T7) antibody (lane 2).
Figure 3:
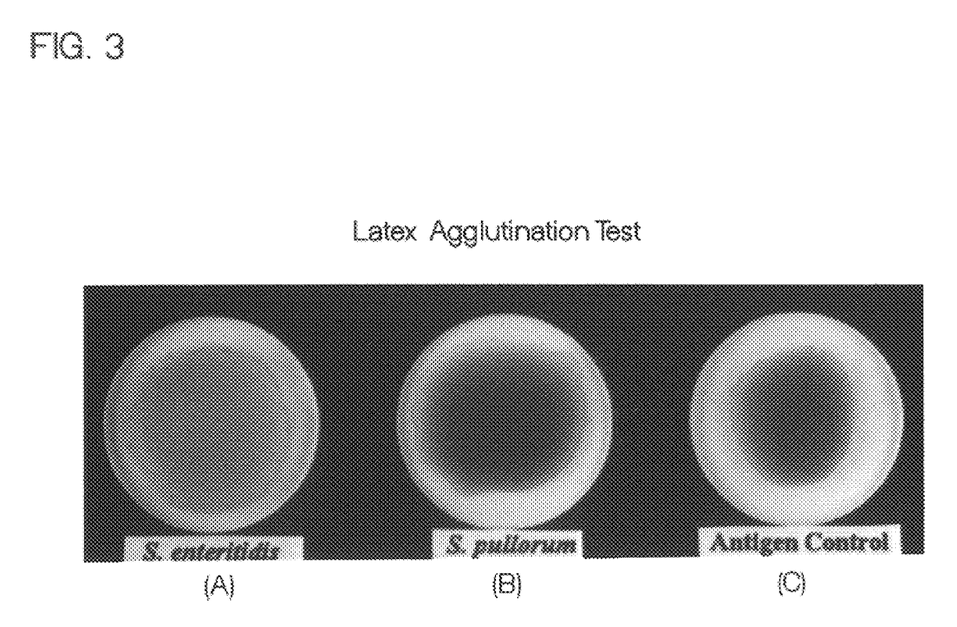
FIG. 3 is a photograph showing results of a rSef14-latex agglutination assay for SE infection in chickens exposed to *S. enteritidis* (A), *S. pullorum* (B), and serum-free antigen control (C).
Figure 4:
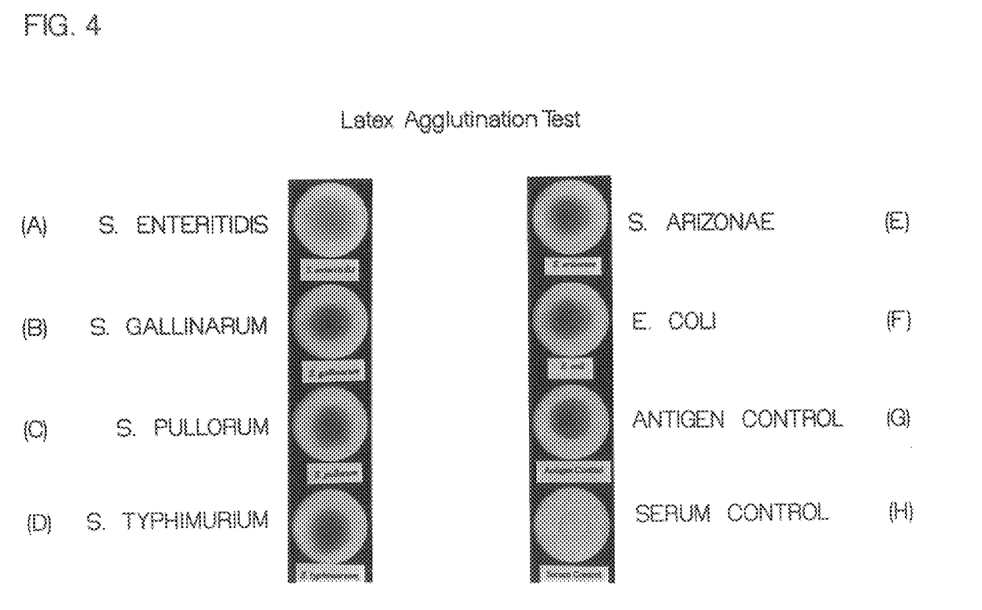
FIG. 4 is a photograph showing results of a rSef14-latex agglutination assay for SE infection in chickens exposed to *S. enteritidis* (A), *S. gallinarum* (B), *S. pullorum* (C), *S. typhimurium* (D), *C. arizonae* (E), *E. coli* (F), serum free antigen control (G), and serum control (H).

The lysates were separated on 12% polyacrylamide gels and transferred onto a nitrocellulose membrane using Trans-blot apparatus (Bio-Rad laboratories, Hercules, Calif.). Following transfer, the membrane was blocked with 3% BSA in phosphate buffered saline (PBS) and stained with either T7 anti-tag antibody (Novagen) or rabbit anti-Sef14 specific antibody (kindly provided by Dr. W. W. Kay, University of Victoria, BC, Canada). The membrane was washed and stained with anti-rabbit IgG/HRP conjugate and treated with developing reagent (Amersham lif sciences, Inc., USA) for 1 minute, exposed to X-ray film, and the radiograph developed. The results are shown in FIG. 2, where lane 1 is probed with anti-Sef14 antibody, and lane 2 with T7 anti-tag antibody.

Purification of rSef14 Fragment Protein by Column Chromatography and Electroelution The recombinant Sef14, protein fragment produced in the cell lysates described above was purified by binding of the Histidine-rich tag to nickel columns as described by the manufacturer (Novagen). Briefly, the cells were induced and extract was prepared as described above except that the induced cells were suspended in Tris buffer without EDTA. The cell lysate was passed through nickel columns and washed sequentially with binding buffer (5 mM imidazole, 0.5 M NaCl, 20 mM Tris-CHl, pH 7.9) and wash buffer (60 mM imidazole, 0.5 M NaCl, 20 mM Tris-HCl, pH 7.9). The bound protein was eluted using elution buffer (1 M imidazole, 0.5 M NaCl, 20 mM Tris-HCl pH 7.9), quantitated using a Bio-Rad protein assay kit (Bio-Rad laboratories, Hercules, Calif.), and analyzed by SDS-PAGE. (See FIG. 1, lane 2, where the arrow indicates the rSef14 fragment at about 19 KDa.) Since the column purified recombinant material contained traces of non-specific proteins, the appropriate rSef14 fragment was further purified by cutting the rSef14 fragment from the gel and electroelution (Bio-Rad) following the manufacturer's suggested protocol. The electroluted fragment is shown in lane 4 of FIG. 1 (at arrow).

Example 3

Covalent Coupling of rSef14 to Blue-dyed Latex Beads

The electroeluted rSef14 protein fragment was coupled to either 0.5 μm or 1.0 μm blue-dyed latex beads (Polysciences Inc., Warrington, Pa.) by gluteraldehyde method. Briefly, 1 ml of 2.5% suspension of the beads were washed with PBS (pH 7.4), pelleted by centrifugation and resuspended in 1 ml of 8% gluteraldehyde (EM grade) in PBS, and incubated overnight with gentle end-to-end mixing at room tempera- ture. Following gluteraldehyde treatment, the beads were pelleted, washed with PBS three times and incubated with 500 μg of purified rSef14 fragment for 5 hours at room temperature with gentle end-to-end mixing. The beads were pelleted, and incubated with 1 ml of 0.5 M ethanolamine in PBS for 30 minutes at room temperature with gentle end-to-end mixing. The mixture was then treated with 1 ml of 10 mg/ml BSA in PBS for 30 minutes at room temperature, centrifuged and the pellet resuspended in 1 ml PBS (pH 7.4), containing 10 mg/ml BSA, 0.1% NaN$_3$ and 5% glycerol, and stored at 4° C. to form rSef14 fragment coated latex beads for use in agglutination assays.

Example 4 rSef14-latex Bead Agglutination Test

Bacteria was administered to chickens by either injection, intratracheal or oral administration of $10^7$ colony forming units (CFU) of either *S. enteritidis, S. pullorum, S. arizonae, S. typhimurium, S. gallinarum,* or *E. coli.* After about two to three weeks exposure, serum was collected and used to evaluate the sensitivity and specificity of the rSef14-latex beads in an agglutination assay for anti-SE antibody binding. A total volume of 7.5 $\mu$l of rSef14 fragment coated latex beads, produced as described for Example 3, were mixed with an equal volume of chicken serum collected from birds exposed to various pathogens, as described above. The presence of agglutination, visually seen as a loss of intense blue color in the sample (i.e., lightening of color as the coated beads agglutinate or form a lattice). Absence of the agglutination reaction was visualized by the remaining intense blue color of the dyed beads in a homogeneous suspension. Positive or negative agglutination reaction was recorded after two minutes. The results are shown in FIGS. 3 and 4.

In FIG. 3, intense blue color (negative result) is seen in test samples B and C (*S. pullorum* and the serum-free antigen control). In contrast, a positive agglutination result is seen in test Sample A, (*S. enteritidis*), as a pale blue, diffuse agglutination pattern.

In FIG. 4, a positive agglutination reaction is seen in sample A (*S. enteritidis*) and in sample H (serum control). No agglutination reaction is seen in the samples B–G containing serum animals exposed to the following pathogens: *S. gallinarium* (B), *S. pullorum* (C), *S. typhimurium* (D), *S. arizonae* (E), *E. coli* (F), and serum free antigen control (H).

Example 5

Detection of anti-S.E. Anitbodies in Infected Chickens

To confirm the specificity of the assay of the invention, forty SPF chickens (age 4 weeks) were innoculated with various species of Salmonella. A suspension of $10^9$ CFU in PBS was administered by injection. A booster dose of $10^9$ CFU was administered orally two weeks later. Serum samples were taken at weekly intervals and assayed for the presence of anti-SE antibodies.

Serum samples were assayed by the standard Serum Plate Test (SPT) as described in Schaffer and MacDonald, 1931, *J Am Vet Med Assoc* 79:236–240. Slides were visually scored (+ or –) for the presence of agglutination, indicating antigen-antibody binding. Samples were also assayed by the Microtiter Plate Test (MPT) as described in Williams and Whittemore, 1971 *Applied Microbiology* 21:394–399. These two assays are standard screening methods for the detection of Salmonella, using *S. pullorium* as a whole-cell antigen, and are not specific for SE, as shown in the table below.

To demonstrate the specificity of the assays of the invention, serum samples were assayed using the latex agglutination test (LAT) described above for Example 4, which utilized the truncated Spf14 antigen coupled to latex beads. Serum samples were also assayed for anti-SE antibodies by ELISA. In the ELISA, the truncated Spf14 antigen prepared as described for Example 3, was coated onto polystyrine plates. Antigen-coated plates were exposed to serum samples to permit binding of anti-SE antibodies to the antigen. The bound antigen-antibody complexes were washed, and then incubated with anti-chicken antibody coupled to biotin. The complex was then exposed to strep-avidin for signal detection.

Results are shown in the table below. The LAT and Elisa assays demonstrated a useful specificity for the detection of SE. Of the organisms tested, only *S.dublin,* a bovine pathogen, demonstrated cross-reactivity in the assays.

| Species | SPT | MT | LAT | ELISA |
|---|---|---|---|---|
| *S. enteritidis* | + | + | + | + |
| *S. gallinarum* | + | + | – | – |
| *S. pullorum* | + | + | – | – |
| *S. dublin* | + | + | + | + |
| *S. berta* | + | + | – | – |
| *S. typhimurium* | – | + | – | – |
| *E. coli* | – | – | – | – |
| Control, (no. cells) | – | – | – | – |

Example 6

Specificity of anti-SE Assay

The ELISA assay for detecting anti-SE antibodies described above for Example 6 was tested for specificity using a panel of antisera against known pathogenic organisms. Each sera was assayed in the anti-SE ELISA. No crossreativity was observed with any of the tested antisera.

| Antisera | ELISA |
|---|---|
| Pox | – |
| Reo | – |
| Rev | – |
| SB-1 | – |
| IBDV | – |
| ILT | – |
| LLA | – |
| LLB | – |
| MS | – |
| MG | – |
| NDV | – |
| CAV | – |
| HVT | – |
| IBV | – |
| *S. typhimurium* | – |
| *S. gallinarum* | – |
| *S. pullorum* | – |

Example 7

Sensitivity of ELISA for Detection of SE

Fifty white leghorn layer chickens (5 weeks old) were orally innoculated in a single exposure with varied amounts of SE, from $10^4$ to $10^{10}$ CFU in PBS. Serum samples were collected at weekly intervals for up to seven weeks. Eggs were collected for egg yolk antibody detection.

Figure 5:
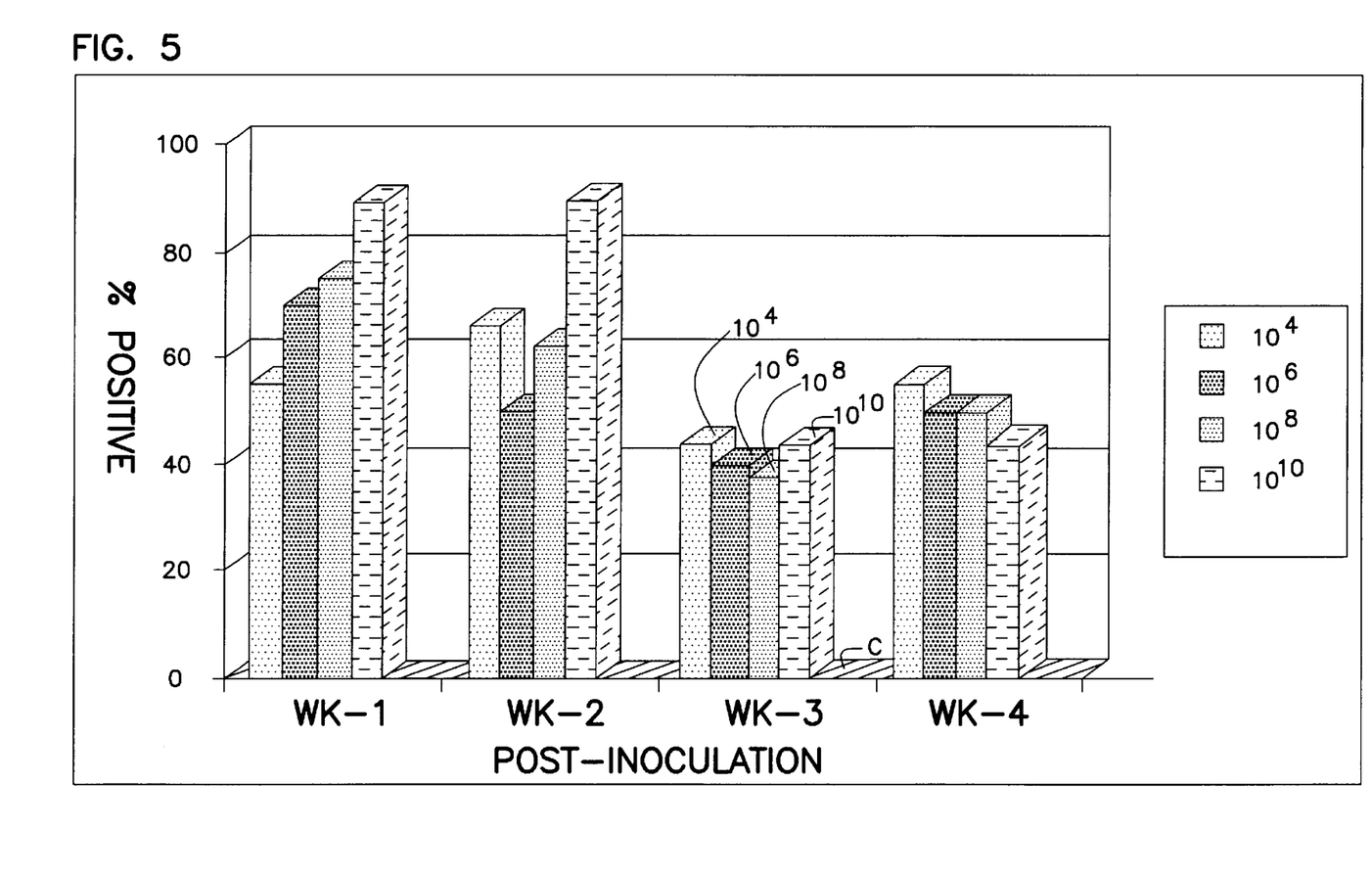
FIG. 5 is a graph showing the percentage of chickens testing positive for anti-SE antibodies during 4 weeks post-innoculation. The five bars at each week represent innoculation with $10^4$, $10^6$, $10^8$, $10^{10}$, and control (no cells).

Samples were analized for detection of anti-SE antibodies using the ELISA described above for Example 6. As shown in FIG. 5, control chickens showed no positive reaction in the ELISA assay. Approximately 40–80% of chickens exposed to $10^4$, $10^6$, $10^8$, and $10^{10}$ CFU of SE tested positive for anti-SE antibodies during the first four weeks post-innoculation. From 4–7 weeks post-innoculation, the data stabilized at about 45% positive detection of anti-SE antibodies.

Figure 6:
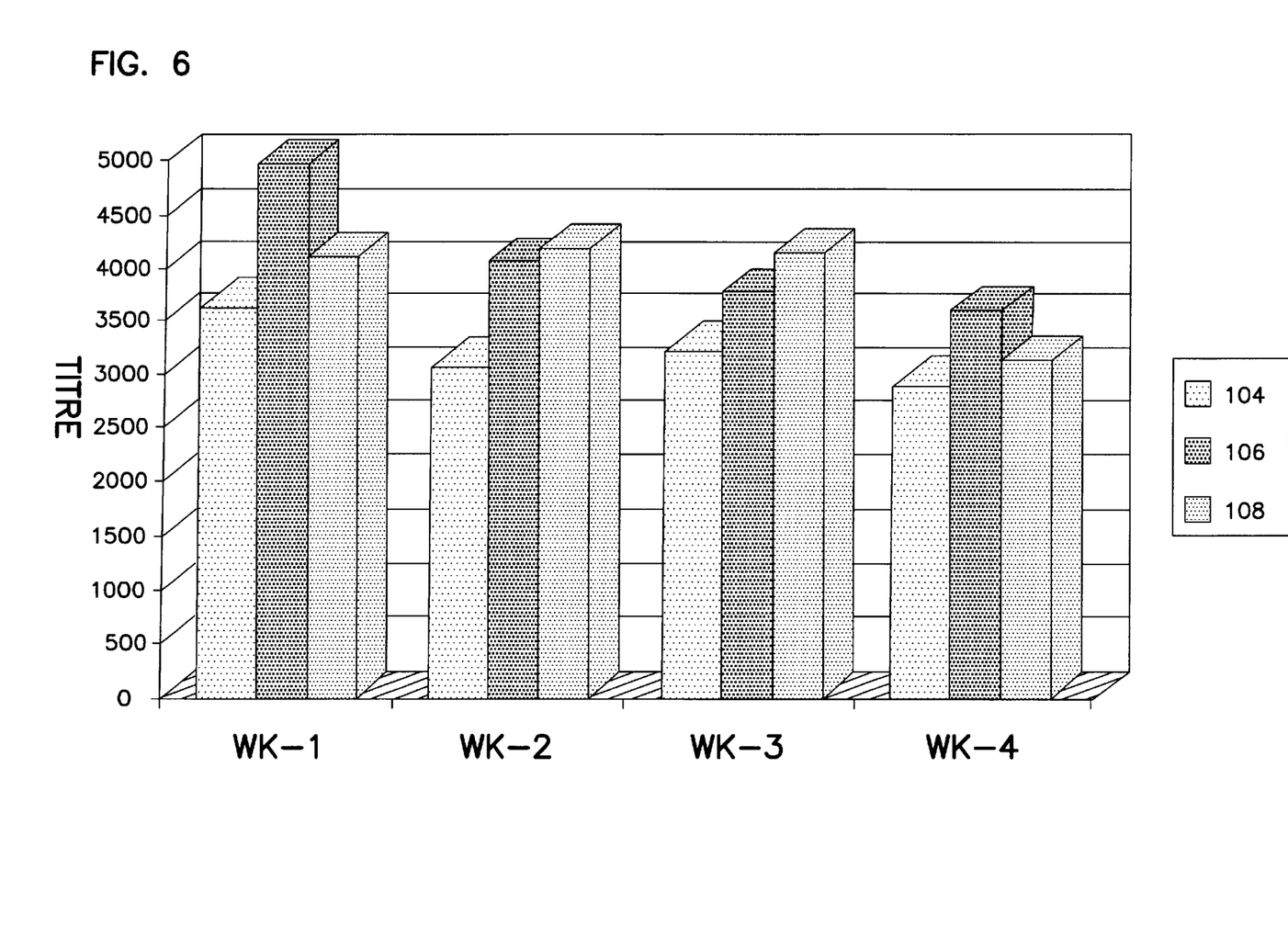
FIG. 6 is a graph showing the antibody titres of chicken sera samples testing positive for anti-SE antibodies.
Figure 7:
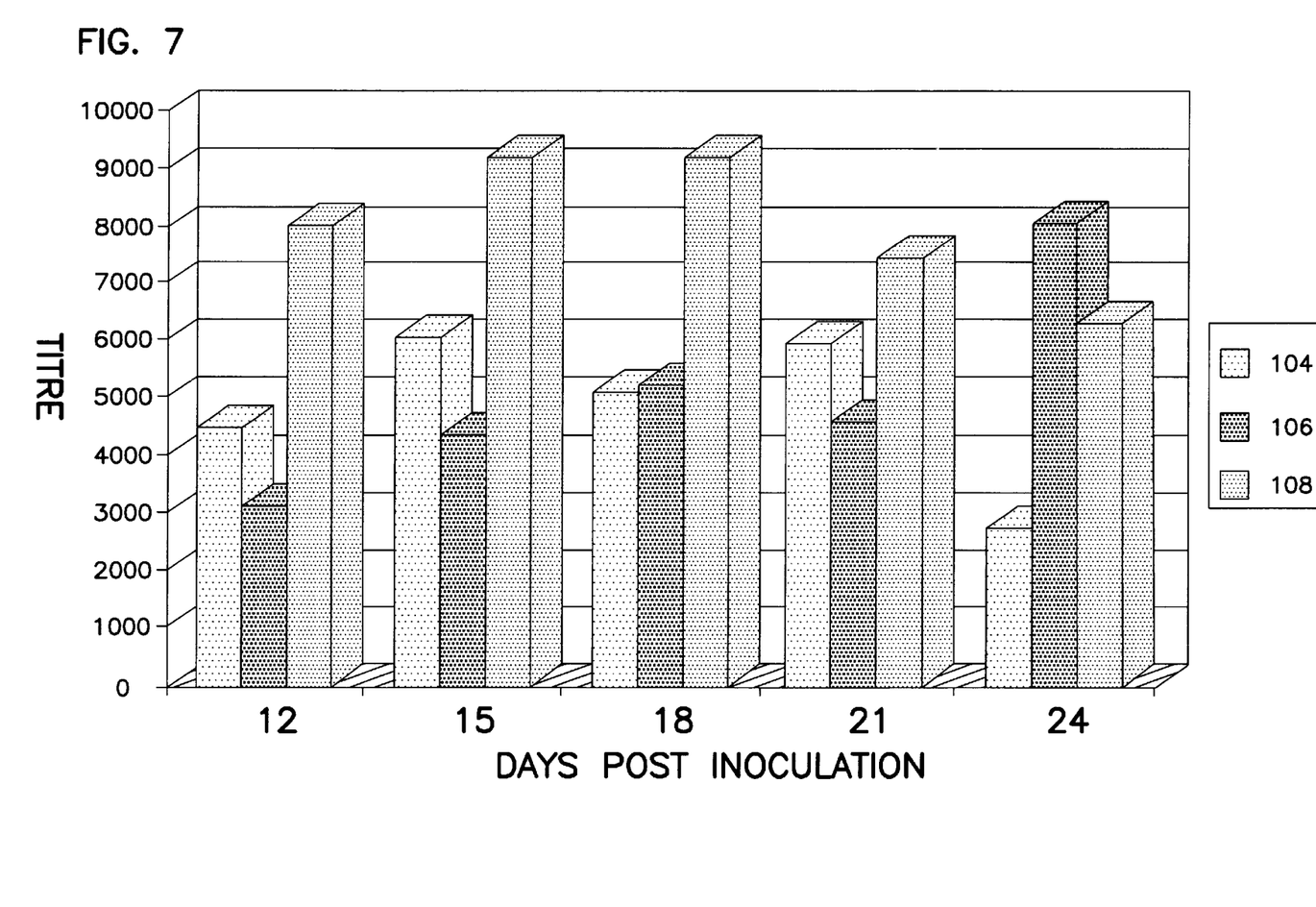
FIG. 7 is a graph showing the antibody titres of chicken egg yolk samples testing positive for anti-SE antibodies.

Antibody titers in the sera and egg yolks of chickens exposed to $10^4$, $10^6$, and $10^8$ CFU of SE and testing positive in the ELISA for anti-SE antibodies are shown in FIGS. 6 and 7.

These data demonstrate specific detection of anti-SE antibodies using recombinant Sef14-antigen coated latex beads in an agglutination assay and using the antigen as a capture agent in an ELISA. These assays provide a sensitive and specific diagnostic tool for the detection of anti-SE antibodies in animals and for the diagnosis of SE infection.

We claim:

1. A method for detecting anti-*Salmonella enteritidis* antibodies in animals, the method comprising:

reacting a sample obtained from an animal with a truncated Sef14 antigen under conditions to permit anti-*Salmonella enteritidis* antibodies to bind the antigen, the truncated antigen having at least the native Sef14 signal peptide removed;

determining the presence or amount of antibody-antigen binding; and correlating antibody-antigen binding with the presence of anti-*Salmonella enteritidis* antibodies in the sample.

2. A method for diagnosing *Salmonella enteritidis* infection in animals, the method comprising:

reacting a sample obtained from an animal with a truncated Sef14 antigen under conditions to permit anti- 
*Salmonella enteritidis* antibodies to bind the antigen, the truncated antigen having at least the native Sef14 signal peptide removed;

determining the presence or amount of antibody-antigen binding; and correlating antibody-antigen binding with *Salmonella enteritidis* infection.

3. The method of claim 1, wherein the truncated Sef14 antigen has the amino acid sequence of Sequence ID. No. 4.

4. The method of claim 1, wherein the truncated Sef14 antigen has the amino acid sequence of Sequence ID. No.6.

5. The method of claim 1, wherein said antigen is fixed to an inert surface prior to said reacting.

6. The method of detecting anti-*Salmonella enteritidis* antibodies described in claim 1, wherein the animal samples are obtained from fowl, and particularly from chickens or turkeys.

7. The method of claim 2, wherein the animal sample is obtained from fowl, and particularly from chickens or turkeys.

8. An assay kit for the detection of anti-*Salmonella enteritidis* antibodies comprising Sef14 antigen fixed to an inert surface, wherein the Sef14 antigen consists essentially of the amino acid sequence of Sequence ID No. 6.

9. The assay kit of claim 8, wherein the antigen consists essentially of the amino acid sequence of Sequence ID. No. 4.

10. The assay kit of claim 8, wherein the antigen is coated on beads.

11. The assay kit of claim 9, wherein the antigen is coated on beads.

12. The assay kit of claim 8, further comprising labeled anti-chicken antibodies.

13. The assay kit of claim 9, further comprising labeled anti-chicken antibodies.

* * * * *

SEQUENCE LISTING

<160> NUMBER OF SEQ ID NOS: 6

<210> SEQ ID NO 1
<211> LENGTH: 27
<212> TYPE: DNA
<213> ORGANISM: Salmonella enteritidis

<400> SEQUENCE: 1
gggaattcgc tggctttgtt ggtaaca                                          27

<210> SEQ ID NO 2
<211> LENGTH: 30
<212> TYPE: DNA
<213> ORGANISM: Salmonella enteritidis

<400> SEQUENCE: 2
gggctcgagt tagttttgat actgaacgta                                       30

<210> SEQ ID NO 3
<211> LENGTH: 552
<212> TYPE: DNA
<213> ORGANISM: Salmonella enteritidis
<220> FEATURE:
<221> NAME/KEY: CDS
<222> LOCATION: (1)..(540)

<400> SEQUENCE: 3 atg ggc agc agc cat cat cat cat cat cac agc agc ggc ctg gtg ccg      48
Met Gly Ser Ser His His His His His His Ser Ser Gly Leu Val Pro
 1               5                  10                  15 cgc ggc agc cat atg gct agc atg act ggt gga cag caa atg ggt cgc      96
Arg Gly Ser His Met Ala Ser Met Thr Gly Gly Gln Gln Met Gly Arg
             20                  25                  30 gga tgg gaa ttc gct ggc ttt gtt ggt aac aaa gca gtg gtt cag gca     144
Gly Trp Glu Phe Ala Gly Phe Val Gly Asn Lys Ala Val Val Gln Ala
         35                  40                  45 gcg gtt act att gca gct cag aat aca aca tca gcc aac tgg agt cag     192
Ala Val Thr Ile Ala Ala Gln Asn Thr Thr Ser Ala Asn Trp Ser Gln
     50                  55                  60 gat cct ggc ttt aca ggg cct gct gtt gct gct ggt cag aaa gtt ggt     240
Asp Pro Gly Phe Thr Gly Pro Ala Val Ala Ala Gly Gln Lys Val Gly
 65                  70                  75                  80 act ctc agc att act gct act ggt cca cat aac tca gta tct att gca     288
Thr Leu Ser Ile Thr Ala Thr Gly Pro His Asn Ser Val Ser Ile Ala
                 85                  90                  95 ggt aaa ggg gct tcg gta tct ggt ggt gta gcc act gtc ccg ttc gtt     336
Gly Lys Gly Ala Ser Val Ser Gly Gly Val Ala Thr Val Pro Phe Val
            100                 105                 110

```
gat gga caa gga cag cct gtt ttc cgt ggg cgt att cag gga gcc aat    384
Asp Gly Gln Gly Gln Pro Val Phe Arg Gly Arg Ile Gln Gly Ala Asn
            115                 120                 125 att aat gac caa gca aat act gga att gac ggg ctt gca ggt tgg cga    432
Ile Asn Asp Gln Ala Asn Thr Gly Ile Asp Gly Leu Ala Gly Trp Arg
130                 135                 140 gtt gcc agc tct caa gaa acg cta aat gtc cct gtc aca acc ttt ggt    480
Val Ala Ser Ser Gln Glu Thr Leu Asn Val Pro Val Thr Thr Phe Gly
145                 150                 155                 160 aaa tcg acc ctg cca gca ggt act ttc act gcg acc ttc tac gtt cag    528
Lys Ser Thr Leu Pro Ala Gly Thr Phe Thr Ala Thr Phe Tyr Val Gln
                165                 170                 175 cag tat caa aac taactcgagc cc                                       552
Gln Tyr Gln Asn
            180

<210> SEQ ID NO 4
<211> LENGTH: 180
<212> TYPE: PRT
<213> ORGANISM: Salmonella enteritidis

<400> SEQUENCE: 4

Met Gly Ser Ser His His His His His His Ser Ser Gly Leu Val Pro
  1               5                  10                  15

Arg Gly Ser His Met Ala Ser Met Thr Gly Gly Gln Gln Met Gly Arg
             20                  25                  30

Gly Trp Glu Phe Ala Gly Phe Val Gly Asn Lys Ala Val Val Gln Ala
         35                  40                  45

Ala Val Thr Ile Ala Ala Gln Asn Thr Thr Ser Ala Asn Trp Ser Gln
     50                  55                  60

Asp Pro Gly Phe Thr Gly Pro Ala Val Ala Gly Gln Lys Val Gly
 65                  70                  75                  80

Thr Leu Ser Ile Thr Ala Thr Gly Pro His Asn Ser Val Ser Ile Ala
                 85                  90                  95

Gly Lys Gly Ala Ser Val Ser Gly Val Ala Thr Val Pro Phe Val
            100                 105                 110

Asp Gly Gln Gly Gln Pro Val Phe Arg Gly Arg Ile Gln Gly Ala Asn
        115                 120                 125

Ile Asn Asp Gln Ala Asn Thr Gly Ile Asp Gly Leu Ala Gly Trp Arg
130                 135                 140

Val Ala Ser Ser Gln Glu Thr Leu Asn Val Pro Val Thr Thr Phe Gly
145                 150                 155                 160

Lys Ser Thr Leu Pro Ala Gly Thr Phe Thr Ala Thr Phe Tyr Val Gln
                165                 170                 175

Gln Tyr Gln Asn
            180

<210> SEQ ID NO 5
<211> LENGTH: 435
<212> TYPE: DNA
<213> ORGANISM: Salmonella enteritidis
<220> FEATURE:
<221> NAME/KEY: CDS
<222> LOCATION: (1)..(432)

<400> SEQUENCE: 5 gct ggc ttt gtt ggt aac aaa gca gtg gtt cag gca gcg gtt act att     48
Ala Gly Phe Val Gly Asn Lys Ala Val Val Gln Ala Ala Val Thr Ile
  1               5                  10                  15
```

-continued

```
gca gct cag aat aca aca tca gcc aac tgg agt cag gat cct ggc ttt      96
Ala Ala Gln Asn Thr Thr Ser Ala Asn Trp Ser Gln Asp Pro Gly Phe
            20                  25                  30 aca ggg cct gct gtt gct gct ggt cag aaa gtt ggt act ctc agc att     144
Thr Gly Pro Ala Val Ala Ala Gly Gln Lys Val Gly Thr Leu Ser Ile
        35                  40                  45 act gct act ggt cca cat aac tca gta tct att gca ggt aaa ggg gct     192
Thr Ala Thr Gly Pro His Asn Ser Val Ser Ile Ala Gly Lys Gly Ala
    50                  55                  60 tcg gta tct ggt ggt gta gcc act gtc ccg ttc gtt gat gga caa gga     240
Ser Val Ser Gly Gly Val Ala Thr Val Pro Phe Val Asp Gly Gln Gly
65                  70                  75                  80 cag cct gtt ttc cgt ggg cgt att cag gga gcc aat att aat gac caa     288
Gln Pro Val Phe Arg Gly Arg Ile Gln Gly Ala Asn Ile Asn Asp Gln
                85                  90                  95 gca aat act gga att gac ggg ctt gca ggt tgg cga gtt gcc agc tct     336
Ala Asn Thr Gly Ile Asp Gly Leu Ala Gly Trp Arg Val Ala Ser Ser
            100                 105                 110 caa gaa acg cta aat gtc cct gtc aca acc ttt ggt aaa tcg acc ctg     384
Gln Glu Thr Leu Asn Val Pro Val Thr Thr Phe Gly Lys Ser Thr Leu
        115                 120                 125 cca gca ggt act ttc act gcg acc ttc tac gtt cag cag tat caa aac     432
Pro Ala Gly Thr Phe Thr Ala Thr Phe Tyr Val Gln Gln Tyr Gln Asn
    130                 135                 140 taa                                                                  435
```

<210> SEQ ID NO 6
<211> LENGTH: 144
<212> TYPE: PRT
<213> ORGANISM: Salmonella enteritidis

<400> SEQUENCE: 6

```
Ala Gly Phe Val Gly Asn Lys Ala Val Val Gln Ala Ala Val Thr Ile
 1               5                  10                  15

Ala Ala Gln Asn Thr Thr Ser Ala Asn Trp Ser Gln Asp Pro Gly Phe
            20                  25                  30

Thr Gly Pro Ala Val Ala Ala Gly Gln Lys Val Gly Thr Leu Ser Ile
        35                  40                  45

Thr Ala Thr Gly Pro His Asn Ser Val Ser Ile Ala Gly Lys Gly Ala
    50                  55                  60

Ser Val Ser Gly Gly Val Ala Thr Val Pro Phe Val Asp Gly Gln Gly
65                  70                  75                  80

Gln Pro Val Phe Arg Gly Arg Ile Gln Gly Ala Asn Ile Asn Asp Gln
                85                  90                  95

Ala Asn Thr Gly Ile Asp Gly Leu Ala Gly Trp Arg Val Ala Ser Ser
            100                 105                 110

Gln Glu Thr Leu Asn Val Pro Val Thr Thr Phe Gly Lys Ser Thr Leu
        115                 120                 125

Pro Ala Gly Thr Phe Thr Ala Thr Phe Tyr Val Gln Gln Tyr Gln Asn
    130                 135                 140
```